United States Patent [19]
Austin et al.

[11] Patent Number: 5,771,900
[45] Date of Patent: Jun. 30, 1998

[54] CONTRACEPTIVE DIAPHRAGM

[75] Inventors: Glenn D. Austin; Theodore J. Colburn; Margaret Z. Kilbourne-Brook, all of Seattle, Wash.; Donald A. Todd, Bedminster, N.J.

[73] Assignee: Path, Seattle, Wash.

[21] Appl. No.: 898,426

[22] Filed: Jul. 22, 1997

[51] Int. Cl.[6] .................................................. A61F 6/06
[52] U.S. Cl. ......................... 128/830; 128/834; 128/837
[58] Field of Search ..................................... 128/830–841

[56] References Cited

U.S. PATENT DOCUMENTS

| | | | |
|---|---|---|---|
| 2,574,767 | 11/1951 | Stubbs | 128/834 |
| 4,381,771 | 5/1983 | Gabbay . | |
| 4,703,752 | 11/1987 | Gabbay . | |
| 4,848,363 | 7/1989 | Cettanach | 128/834 |
| 4,858,624 | 8/1989 | Shihata . | |
| 4,895,170 | 1/1990 | Tlapek | 128/837 |
| 4,989,618 | 2/1991 | Shihata . | |
| 5,207,232 | 5/1993 | Shihata . | |

FOREIGN PATENT DOCUMENTS

| | | | |
|---|---|---|---|
| 595017 | 3/1960 | Canada | 128/837 |

*Primary Examiner*—Michael A. Brown
*Attorney, Agent, or Firm*—Banner & Witcoff, Ltd.

[57] ABSTRACT

A contraceptive diaphragm having a rim surrounding a thin membrane, the membrane having a cervical dome extending downwardly from a posterior portion of the membrane. The rim has two curvilinear bands joined together at their respective ends and encased in a coil spring. The shape of the bands creates a rim which curves slightly upwardly at the anterior end of the diaphragm and slightly downwardly at its posterior end. The rim is formed with a curvilinear profile which provides an advantageous fit. A small dome projects upwardly from an anterior portion of the membrane which is grasped by the wearer to remove the diaphragm.

23 Claims, 8 Drawing Sheets

CONTRACEPTIVE DIAPHRAGM

FIELD OF THE INVENTION

The present invention is directed to contraceptive diaphragms, and more particularly to contraceptive diaphragms having a contoured shaped rim.

BACKGROUND OF THE INVENTION

Contraceptive diaphragms, or simply diaphragms, have been used in their current form for over one hundred years. They are classified as an intra-vaginal barrier contraceptive, although they are commonly used in conjunction with spermicide.

Diaphragms typically consist of an outer rim which defines a generally planar loop having a diameter on the order of 55 to 95 mm, and a dome-shaped membrane which extends across the interior of the rim to form a barrier. The dome-shaped membrane is typically 0.2 to 0.3 mm thick and attached along a central, transverse axis of the rim. The rim and dome are usually made of latex rubber, but have been produced from other inert medical grade elastomers, such as silicone, urethane, vinyl, or thermoplastic elastomer (TPE). The rim has a generally cylindrical cross section which houses a spring that provides stiffness when folding or squeezing for insertion, and which opens the device after insertion. The spring is ordinarily in the form of either a single length of spring coil joined at its ends or a band of spring material.

The Milex wide-seal diaphragm is an alternative diaphragm of silicone construction which is available in the United States through physicians or clinics. This diaphragm has a traditional design except for the projection of an additional lip extending perpendicular from the rim. The lip is provided in an effort to keep the device in place by causing suction between the lip and vaginal mucosa. The device is also purported to be less messy since the wide lip helps keep spermicidal jelly or cream within the diaphragms's concave surface.

In use, the diaphragm is inserted into the vagina so that the proximal end wedges in the posterior fornix behind the cervix and the distal end wedges behind the pubic notch. This wedged fit is intended to maintain coverage of the cervix during intercourse. However, there are a number of problems associated with the conventional diaphragm design. For instance, due to elongation of the vagina during sexual arousal and coitus, and axial movement of the cervix during various stages of the menstrual cycle, current diaphragms can move from their intended position leading to gaps around the edges of the diaphragm and compromising the barrier provided around the cervix. Accordingly, this type of contraceptive has suffered relatively high contraceptive failure rates of 13 to 17%. To enhance protection, diaphragm users are instructed to place a spermicidal material inside the dome and along the rim for contraceptive protection. Further, a number of various sizes are needed, which not only increases inventory concerns but also requires careful fitting by experienced clinicians in clinical settings. Users have also experienced difficulty in insertion and removal, discomfort including a false sense of "urgency" to urinate due to pressure on the urethra after extended wear, possible increased risk of urinary tract infections, discomfort for the sexual partner during coitus, unpleasant odor from the latex material over time, and deterioration of latex material over time if not carefully maintained.

Another intra-vaginal barrier contraceptive device is the cervical cap. The cervical cap typically is thimble shaped with a heavy rim and a deep rounded dome. It is typically made of latex, although it could be made of other elastomers such as silicone. The cervical cap fits closely around the cervix in the cervical fornix and functions as a barrier to entry of sperm into the cervical os and uterus. However, the cap is difficult for many women to insert and remove as it requires the ability to handle the device deep inside the vagina. Some women have difficulty even touching their own cervix much less manipulating the cap. Removal of the cervical cap is complicated by the fact that a strong suction is formed which must be broken by twisting or prying the rim of the cap. The cervical cap is typically made in four to six different sizes and is fitted initially by a clinician. Due to its difficulty of use, the cervical cap has not been popular.

It is an object of the present invention to provide an improved contraceptive diaphragm which reduces or wholly overcomes some or all of the aforesaid difficulties inherent in prior known devices. Particular objects and advantages of the invention will be apparent to those skilled in the art, that is, those who are knowledgeable and experienced in this field of technology, in view of the following disclosure of the invention and detailed description of certain preferred embodiments.

SUMMARY OF THE INVENTION

The principles of the invention may be advantageously used to provide a contraceptive diaphragm having a contoured shape and improved construction to facilitate insertion and removal, and improve adherence of the diaphragm within the anatomy of a woman.

In accordance with a first aspect, a diaphragm comprises a rim having an anterior portion which curves upwardly and a posterior portion which curves downwardly, a membrane extending within the rim, and a cervical dome extending downwardly away from the posterior portion of the membrane. With this construction, the user obtains a well fit diaphragm which reduces the risk of forming gaps and increases the comfort for the user and her sexual partner. Moreover, the present diaphragm can accommodate wide variations in a woman's anatomy which enables a reduction in the inventory and eases precise fitting concerns.

In accordance with another aspect, the diaphragm further comprises a small removal dome extending upwardly from the anterior portion of the membrane. This feature enables the diaphragm to be more easily manipulated and removed.

In accordance with another aspect, projections are formed along lateral portions of the rim to improve handling of the contraceptive diaphragm.

From the foregoing disclosure, it will be readily apparent to those skilled in the art, that is, to those who are knowledgeable or experienced in this area of technology, that the present invention provides a significant technological advance. Substantial advantage is achieved by providing contraceptive diaphragms having such construction. In particular, increased comfort and ease of insertion is achieved. These and additional features and advantages of the invention disclosed here will be further understood from the following detailed disclosure of certain preferred embodiments.

BRIEF DESCRIPTION OF THE DRAWINGS

Certain preferred embodiments are described in detail below with reference to the appended drawings wherein.

The figures referred to above are not drawn necessarily to scale and should be understood to present a simplified representation of the invention, illustrative of the basic principles involved. Some features of the contraceptive diaphragm depicted in the drawings have been enlarged or distorted relative to others to facilitate explanation and understanding. The same reference numbers are used in the drawings for similar or identical components and features shown in various alternative embodiments. Contraceptive diaphragms as disclosed below, will have configurations and components determined, in part, by the intended application and environment in which they are used.

DETAILED DESCRIPTION OF CERTAIN PREFERRED EMBODIMENTS

Unless otherwise stated, or otherwise clear from the context below, directional references used here are based on the orientation of components and assemblies shown in the appended drawings.

Figure 1:
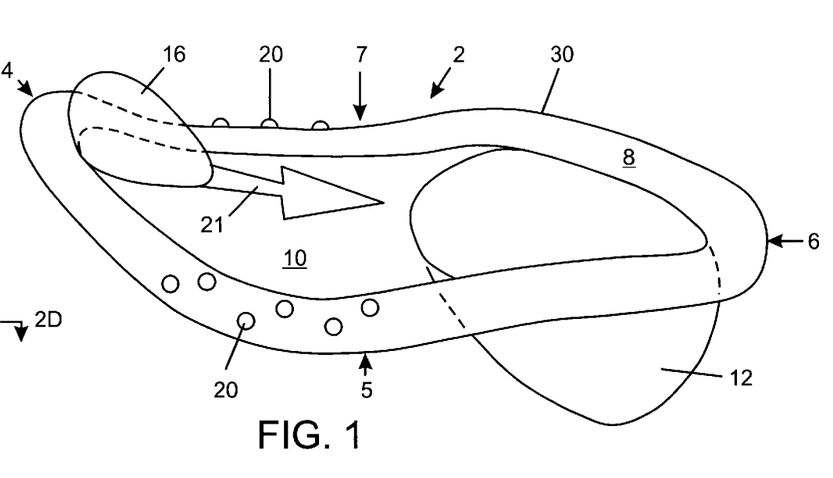
FIG. 1 is a schematic perspective view of a contraceptive diaphragm of the present invention.

A first preferred embodiment of a contraceptive diaphragm, generally designated by the reference numeral 2, is shown in FIG. 1. Diaphragm 2, having anterior portion 4, posterior portion 6, and lateral portions 5, 7, comprises a rim 8 which defines a loop that surrounds a membrane 10 and a cervical dome 12. Membrane 10 is preferably attached to rim 8 such that the plane of membrane 10 is substantially normal to rim 8 along its periphery (FIGS. 2A–2D). The membrane 10 preferably has a thickness of about 0.002–0.012 inches, and is most preferably about 0.008 inches thick. Although the membrane is relatively flat, it has some contour on account of its attachment to the rim which, as described below, has a curvilinear construction. The use of such a thin membrane composed of an elastomeric material enables the membrane to be extremely compliant in order to better cling to vaginal tissues when in use. Nevertheless, due to its thin construction and contoured shape, the diaphragm does not develop an overly aggressive suction.

Cervical dome 12 is a cup-shaped member which extends downwardly from membrane 10 in the posterior portion 6 of diaphragm 2 (FIGS. 1–2, 2A–2D, and 3). In an alternative embodiment, cervical dome 12' may be offset slightly from rim 8 to aid the engagement of diaphragm 2 with the posterior fornix (FIG. 2E). In either embodiment, the dome opens upward to be received over the cervix and close the cervical os. Membrane 10 and dome 12 are preferably formed of silicone, but other suitable materials such as thermoplastic elastomer (TPE), latex, or urethane could be used.

Figure 2:
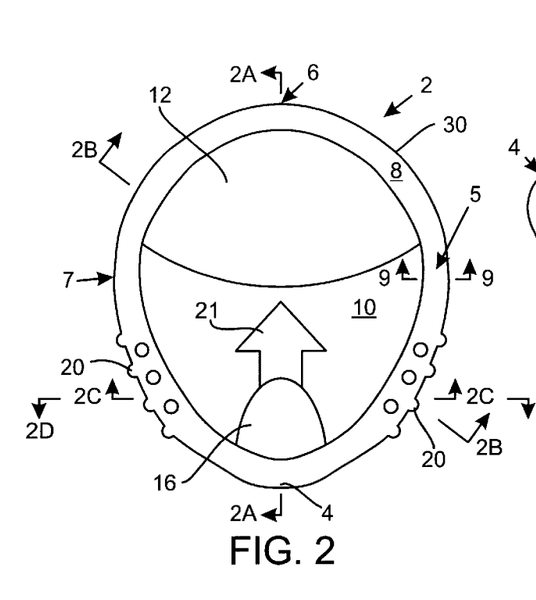
FIG. 2 is a schematic plan view of the contraceptive diaphragm of FIG. 1.
Figure 3:
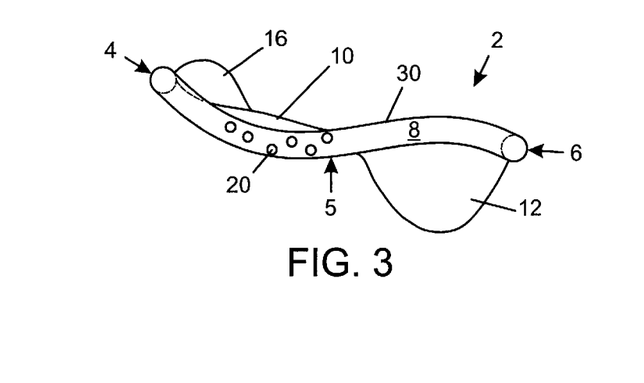
FIG. 3 is a schematic elevation view of the contraceptive diaphragm of FIG. 1.
Figure 10:
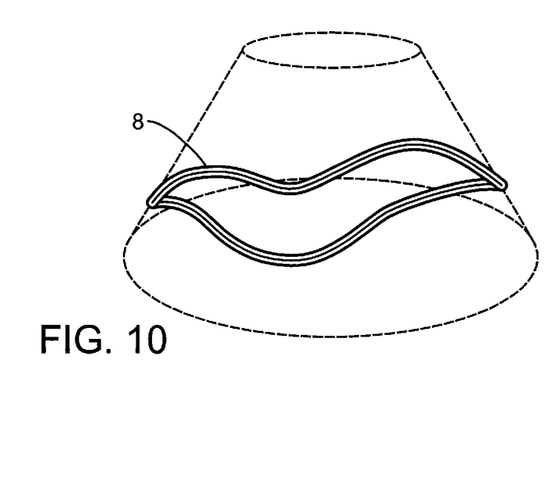
FIG. 10 is a schematic illustration of the rim which conforms to a comic projection.

Rim 8 defines a loop which is preferably substantially elliptical, and nearly circular, in shape when viewed from above (FIG. 2). As can be seen in FIGS. 1 and 3, the profile of rim 8 is not planar like that of a standard diaphragm. Rather, rim 8 has a curvilinear construction with changing radiuses in an axial direction. In the preferred construction, rim 8 conforms to the shape of a conic projection (FIG. 10). Rim 8 along anterior portion 4 of the diaphragm has a centerline contour which curves slightly upwardly thereby reducing interference with the partner and relieving pressure on the urethra that may occur with a standard round, planar ring rim. Rim 8 along posterior portion 6 has a centerline contour which curves slightly downwardly thereby providing for better fit in the fornix surrounding the proximal portion of the cervix. The contours of the rim 8 allow the lateral anterior quadrants of the diaphragm 2 to securely engage supportive tissue in the vagina via shallow embedment in the vaginal wall adjacent to supportive muscle or connective tissue. The gentle arcs of the rim along anterior and posterior portions 4, 6 also provide better engagement, or clinging, of the thin membrane 10 to the vaginal tissue. A single diaphragm 2 can replace five or more sizes of standard diaphragms since its shape and construction allows it to advantageously conform and cling to the anatomy of the vagina. The diameter, or size, of one preferred embodiment of diaphragm 2 is 70 mm which would typically fit women who use standard diaphragms having sizes of 65 mm to 85 mm.

Diaphragm 2 has a reduced bulk when compared to standard diaphragms due to the fact that cervical dome 12 extends from only the posterior portion 6 of the diaphragm whereas the domes of a standard diaphragm extends across the entire rim. The reduced bulk and contoured shape of diaphragm 2 advantageously aid overall handling, increase reliability, reduce stress on the cervix when in position, make the diaphragm easier to store and more inviting to wear, increase partner acceptability, and ease insertion and removal of the diaphragm into and from the introitus. Such a construction also lowers production costs due to the reduced volume of material used.

Figure 2A:
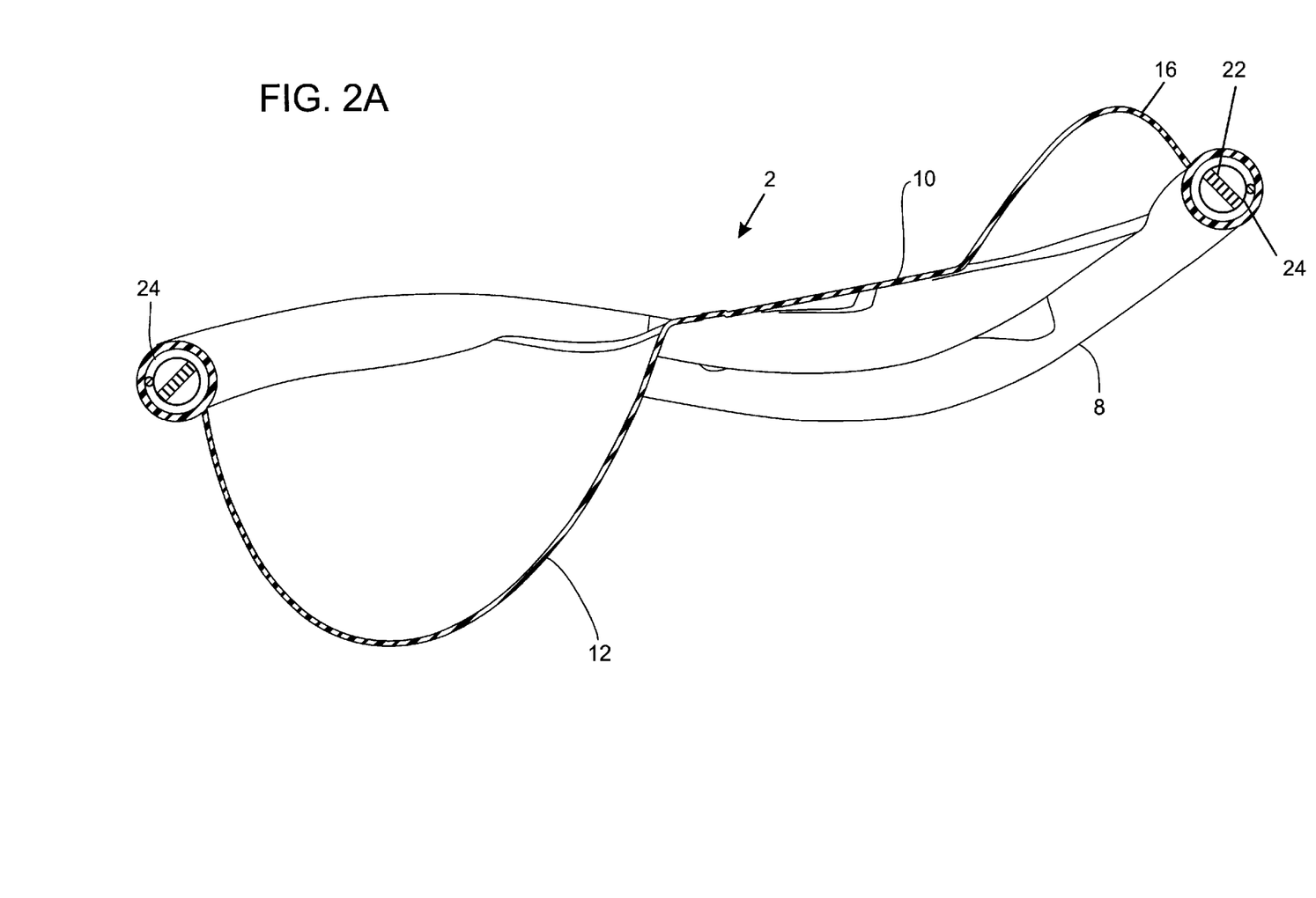
FIG. 2A is a cross-sectional view taken along line 2A—2A in FIG. 2.
Figure 2B:
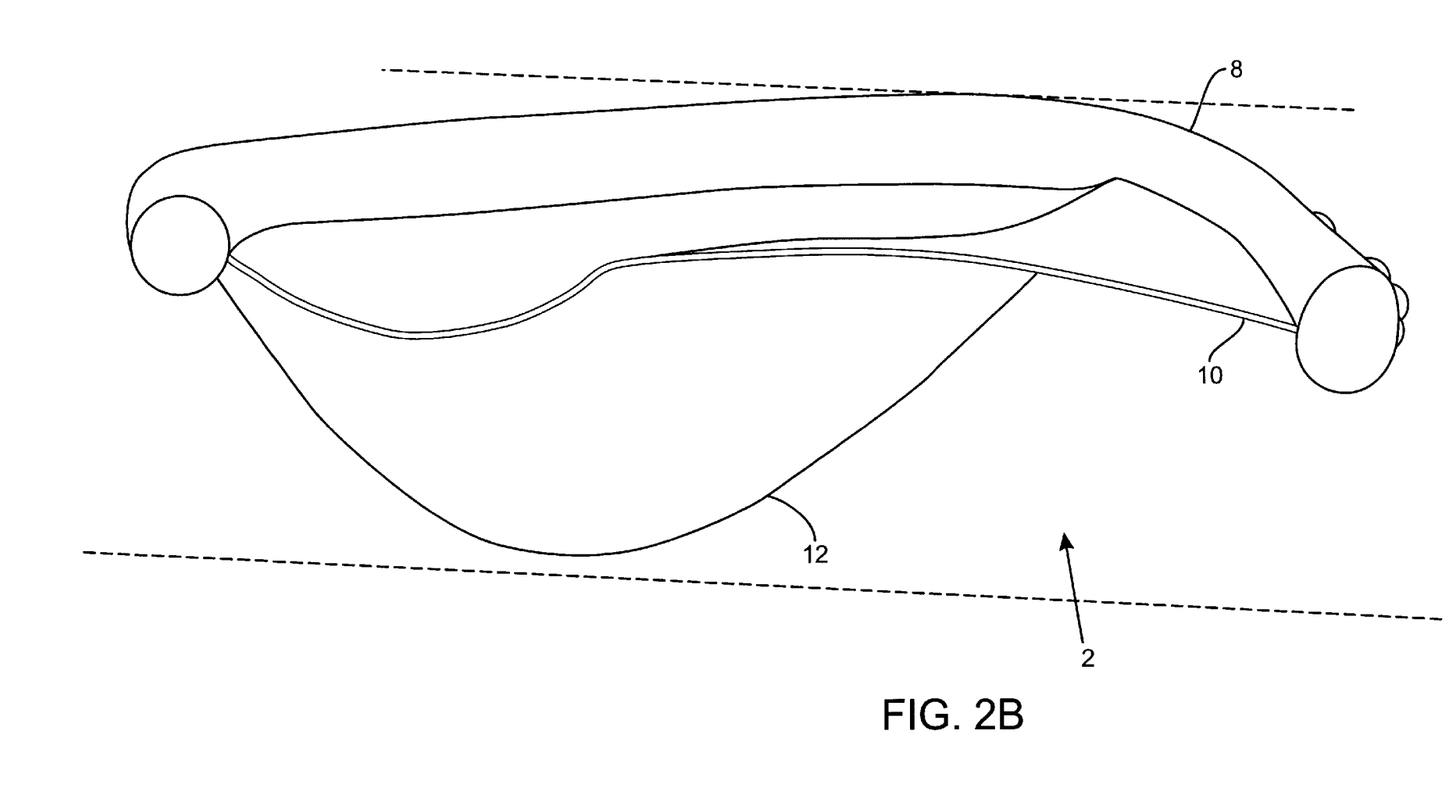
FIG. 2B is a cross-sectional view taken along line 2B—2B in FIG. 2.
Figure 2C:
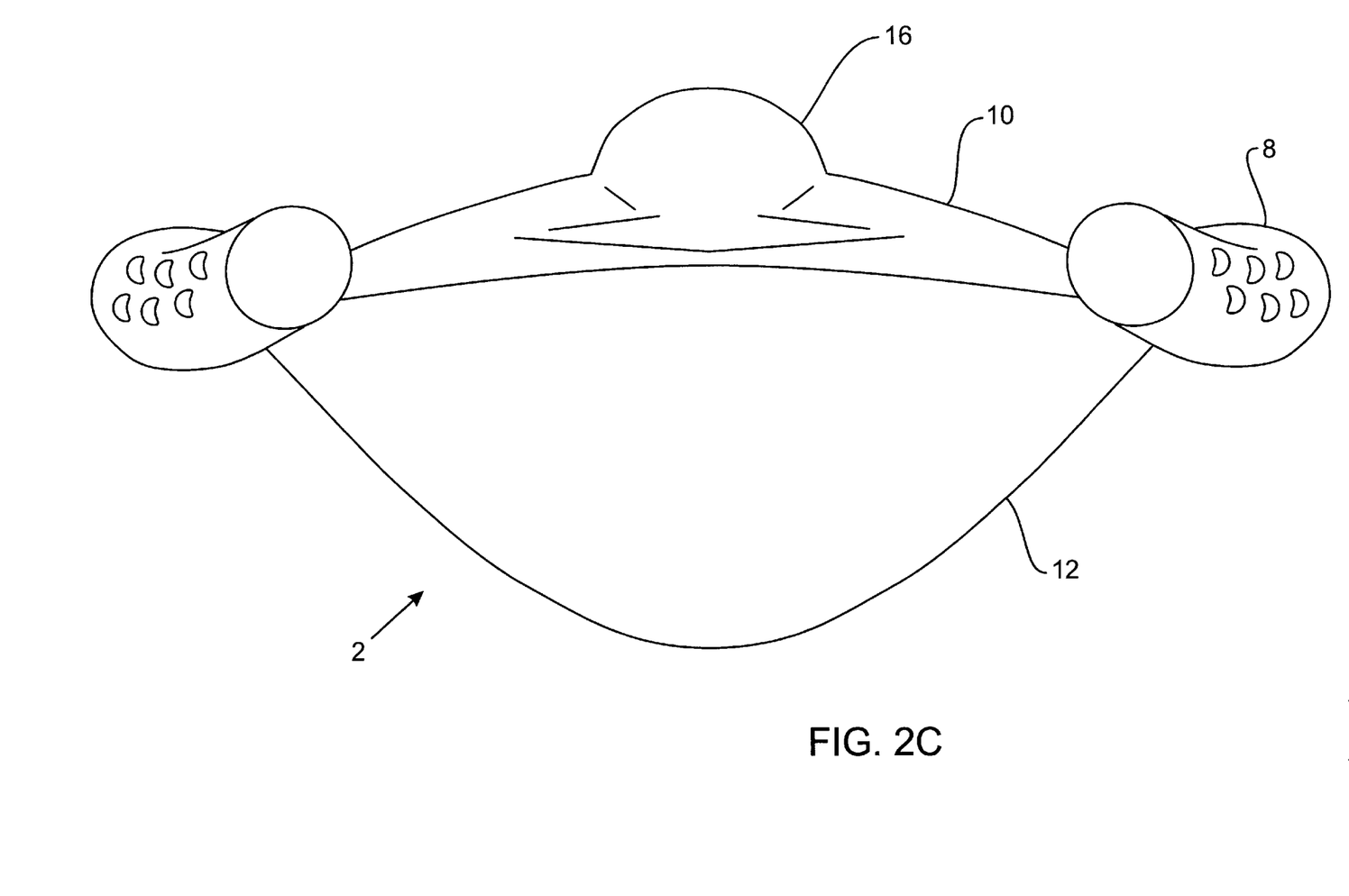
FIG. 2C is a cross-sectional view taken along line 2C—2C in FIG. 2.
Figures 2D, 2E:
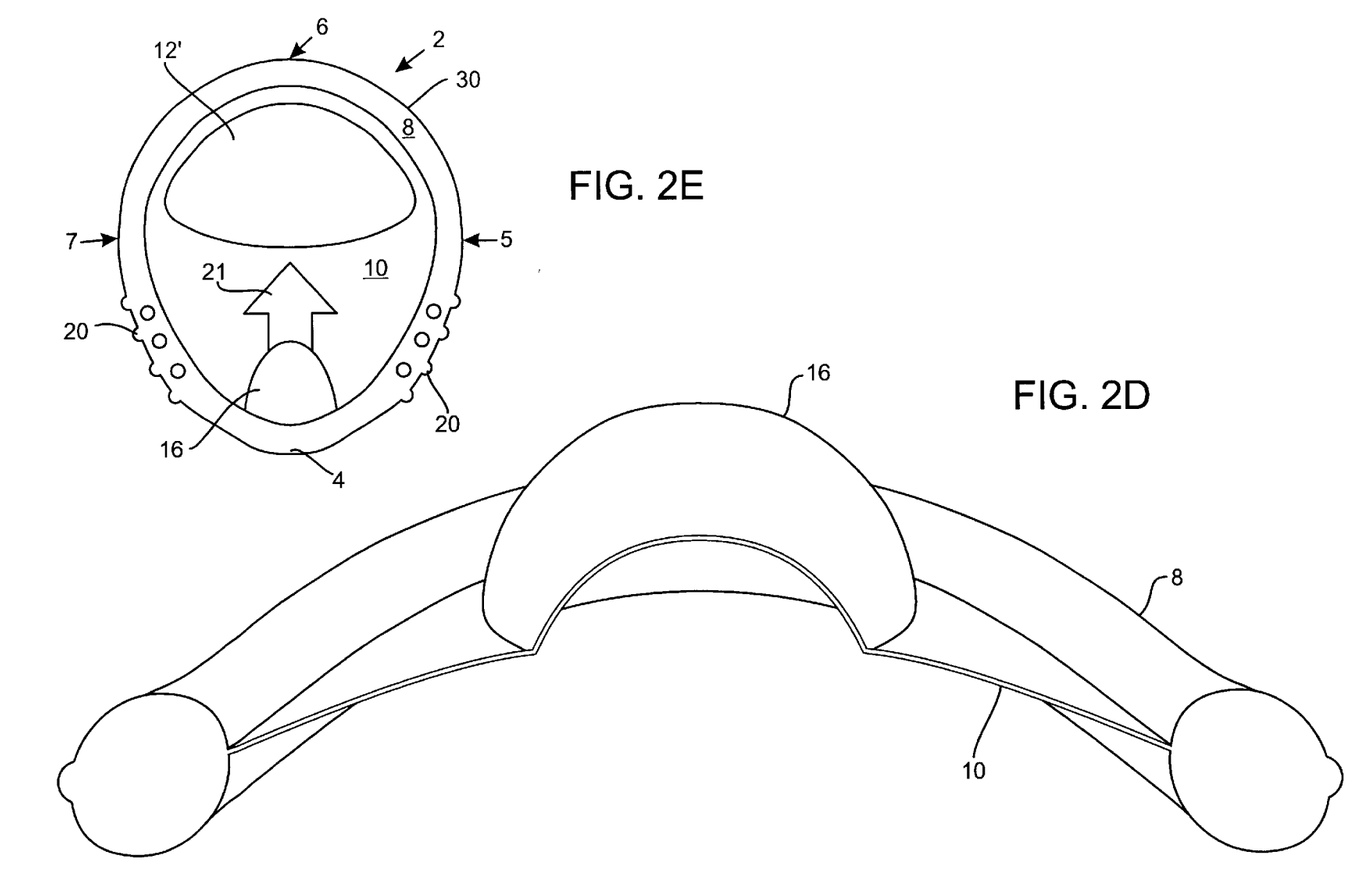
FIG. 2D is a cross-sectional view taken along line 2D—2D in FIG. 2.
FIG. 2E is a top plan view of an alternate construction of the diaphragm.
Figure 4:
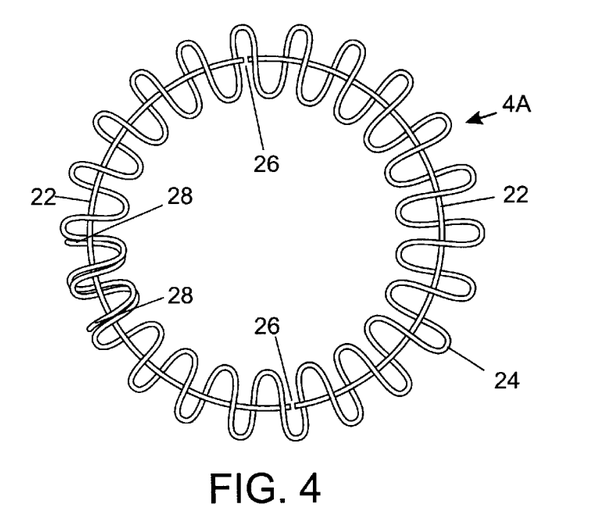
FIG. 4 a schematic plan view of a pair of bands wrapped in a coil spring of the diaphragm of the present invention.
Figure 4A:
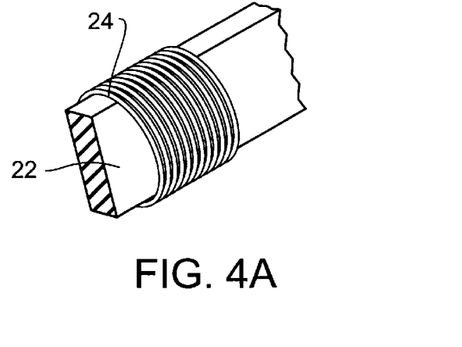
FIG. 4A is an enlarged portion of the bands illustrated in FIG. 4.
Figure 9:
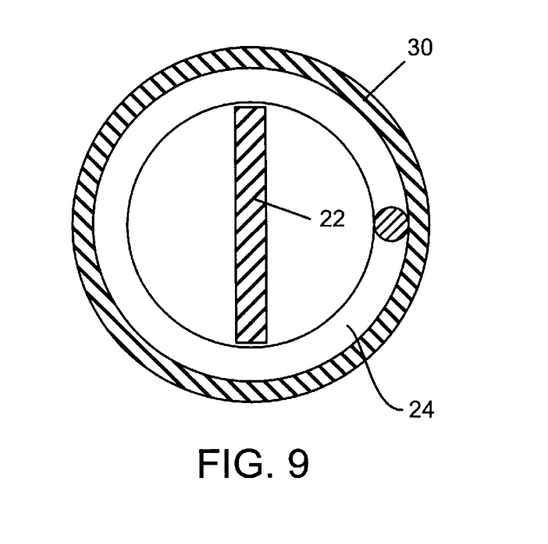
FIG. 9 is a schematic section view taken along line 9—9 of FIG. 2 showing the band and spring assembly encased within the cover of the present invention.

Rim 8 is preferably formed of two curvilinear flat bands 22, a spring 24, and a cover 30. As seen in FIG. 4, the ends of each band abut the ends of the other band to form a loop. A single length open-coil compression spring 24 tightly surrounds the bands 22 to completely enclose the bands at their ends, and thereby form hinge joints 26. The spring 24 is spread out for illustration of the overall construction in FIG. 4. The spring 24, however, is preferably much more tightly wound about the bands to form a close coil or closed coil spring (FIG. 4A). The bands also are preferably contoured such that the flats of the bands pitch (rotate) around the common center-line axis of the band, coil, and rim (FIG. 2A). See, for example, the orientations of the band in FIGS. 2A and 9. The bands 22 are preferably formed of thick spring grade stainless steel having a thickness of preferably about 0.15 mm to about 0.42 mm, and most preferably about 0.25 mm. However, spring grade polymers (e.g., acetal resin), other spring metals, or other suitable materials could be used. Coil spring 24 is preferably made of open coil stainless steel, although other springs could be used. For example, springs of other suitable materials such as spring metals, or even springs which are integrated with the bands in a molded polymer ring structure could be used. Coil spring 24 is preferably formed with a 17 to 22 gauge wire. The inside diameter of the coil spring 24 fits closely around the width of the flat bands 22 in order to maintain the integrity of the hinge joints 26 (FIGS. 2A, 4A and 9). The ends 28 of the coil spring 24 may be butt jointed or, as shown, partially wound together along their common helical path (FIG. 4). The ends 28 of the coil spring 24 are located remote from and preferably 90° from the hinge joints 26, thereby allowing free range of motion of the hinge joints.

The band and spring assembly is encased within cover 30, as seen in FIGS. 1–3 and 9. Cover 30 is generally a flexible tube-like member formed of micro-injection molded medical-grade silicone rubber or other elastomeric material such as latex, TPE, urethane, vinyl or other suitable material. Cover 30 preferably has a Shore A 30 to 60 hardness. Cover 30 is typically premolded to match the shape of the spring and may have a cross section of various configurations including circular, elliptical, or rectangular with rounded corners.

Figure 5:
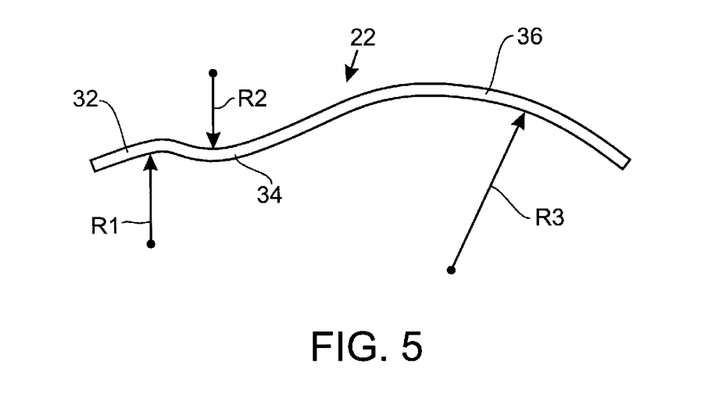
FIG. 5 is a schematic plan view of a band of the present invention.

In a preferred embodiment, each band 22 when flat, as seen in FIG. 5, has a sinusoidal S shape formed of three arcs each having different radii and alternating aspects, or orientations. The first arc 32, at the anterior end 4 of the diaphragm, is concave downward with a radius of curvature R1 of preferably between about 0.6–2.0 inches. The second arc 34 is concave upward with a radius of curvature R2 of preferably between about 0.4–1.6 inches. The third arc 36, at the posterior end 6 of the diaphragm, is concave downward with a radius of curvature R3 of preferably between about 0.9–3.0 inches. In one preferred construction, the first arc 32 has a radius of curvature R1 of about 1.2 inches, the second arc 34 has a radius of curvature R2 of about 0.873 inches, and the third arc 36 has a radius of curvature R3 of about 1.9 inches. The arcs 32, 34, and 36 may be tangent to one another or they may be connected using spline geometry such as non-uniform rational B splines (NURBS).

Figures 6, 7:
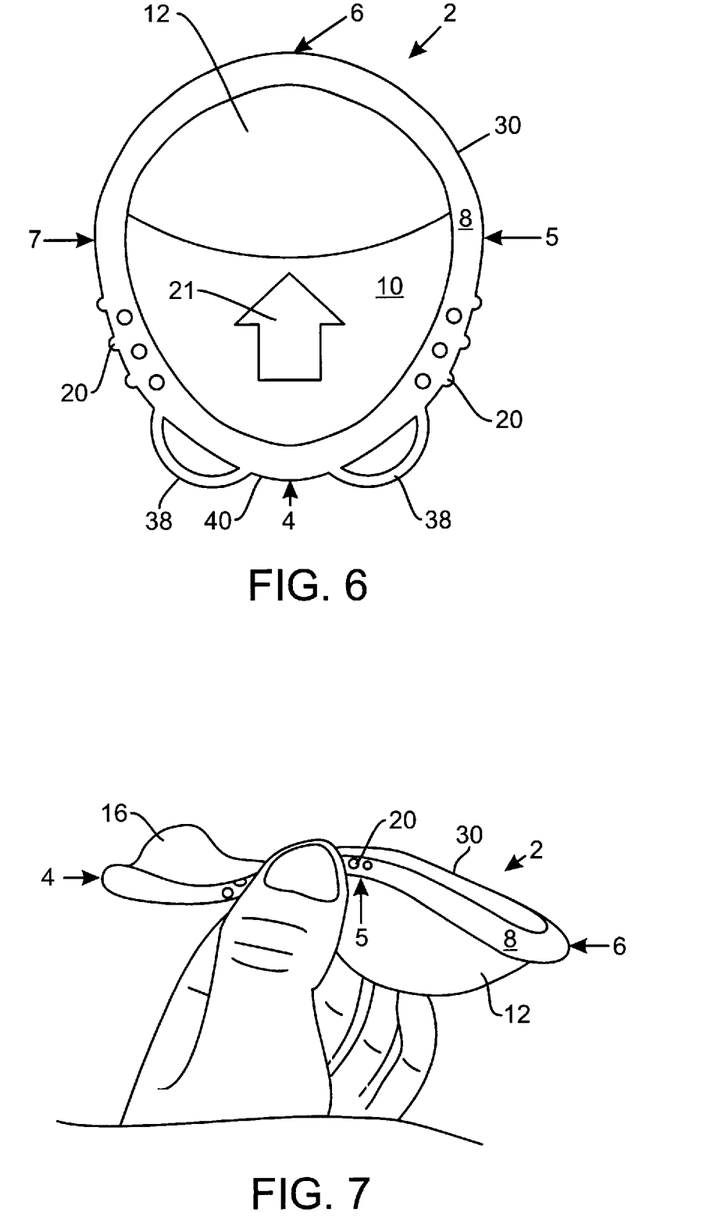
FIG. 6 is a schematic plan view of an alternative embodiment of a contraceptive diaphragm of the present invention.
FIG. 7 is a schematic elevation view of a user grasping the contraceptive diaphragm of the present invention.
Figure 8:
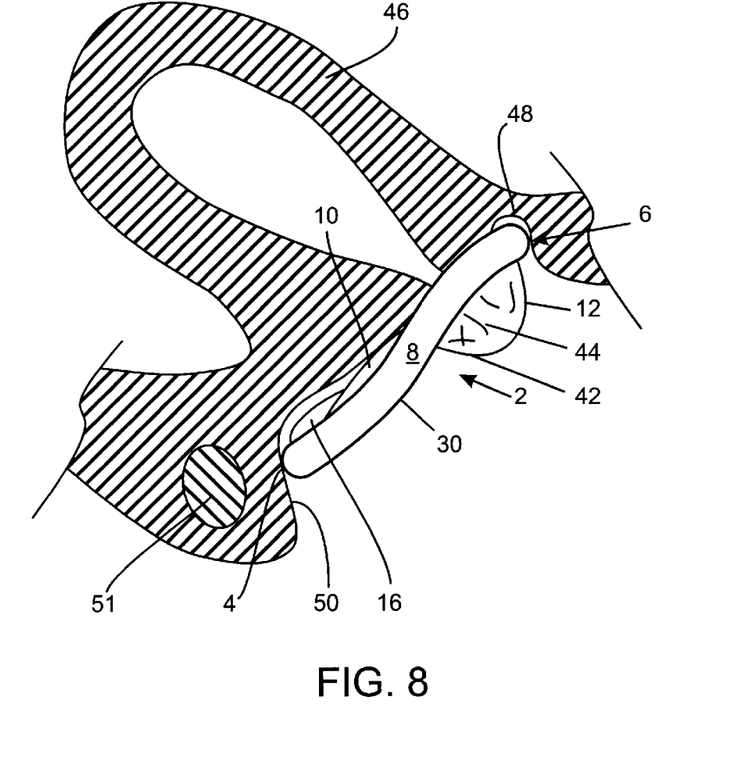
FIG. 8 is a schematic partial section view showing a contraceptive diaphragm of the present invention in use.

When inserting diaphragm 2, as can be seen in FIG. 7, it is grasped about lateral portions 5, 7 and squeezed. The bending dynamics caused by the contoured shape of rim 8 and the functioning of hinge joints 26 changes the shape of diaphragm 2 thereby optimizing the shape of the diaphragm for insertion. Its squeezed shape is more stable and the leading edge for insertion, that is posterior portion 6, is bent downwardly even more so that it more easily passes the anterior aspect of the cervix as the diaphragm is nestled into place. The interaction of coil spring 24 with hinge joints 26 allows diaphragm 2 to flex at the hinge joints thereby reducing the profile of the diaphragm and making its insertion less noticeable and making its deployment within the vagina more effective. Once the diaphragm 2 is in place, coil spring 24 works with bands 22 to restore diaphragm 2 to its original shape. As seen in FIG. 8, when in place, cervical dome 12 fits snugly around cervix 42 covering cervical os 44 of uterus 46. Posterior portion 6 fits snugly into posterior fornix 48.

In one preferred embodiment, cup shaped projection or finger dome 16 opens downwardly from membrane 10 in the anterior portion 4 of diaphragm 2. Finger dome 16 is provided to ease removal of diaphragm 2. As seen in FIG. 8, finger dome 16 is located adjacent the anterior vaginal wall 50 slightly behind pubic bone 51 such that it can be easily grasped or hooked with a finger for removal. Also, since the finger dome 16 is composed of pliable material, the dome tends to collapse and thereby conform to the woman's internal anatomical structure. As discussed above, the upwardly curving anterior portion 4 lifts rim 8 helping to avoid an obstruction for the wearer's partner and relieving pressure on the urethra. To remove diaphragm 2 a finger is inserted into finger dome 16 and the diaphragm is then pulled from the vagina. This embodiment may provide less interference with vaginal anatomy in smaller size vaginas, i.e., those of women normally wearing 60 mm to 70 mm diaphragms.

In yet another preferred embodiment, small dome shaped projections 20 are provided along a portion of lateral portions 5, 7 of rim 8. Projections 20 preferably have a height of 0.5–2.5 mm and a diameter of 1.0–3.0 mm, and are most preferably 1.5 mm high with a diameter of 2 mm. Projections 20 provide a tactile indication of the optimal location for grasping the diaphragm 2 as well as improved grip when inserting the diaphragm into the vagina, especially when it is made slippery by the application of spermicide, gel or other lubricants.

In another preferred embodiment, indicator 21 is provided on membrane 10 to indicate to an individual the direction in which the diaphragm 2 should be inserted. Indicator 21 may be, as shown, an arrow embossed on the surface of membrane 10, or any other suitable means for indicating that posterior portion 6 is inserted firstly into the vagina.

In yet another preferred embodiment, shown in FIG. 6, a pair of loops 38 extend from anterior portion 4 of diaphragm 2. Loops 38 work in a manner similar to finger dome 16 to ease removal of the diaphragm from the vagina. Notch 40, the region formed between loops 38 provides a finger rest during insertion of the diaphragm 2.

In light of the foregoing disclosure of the invention and description of certain preferred embodiments, those who are skilled in this area of technology will readily understand that various modifications and adaptations can be made without departing from the true scope and spirit of the invention. All such modifications and adaptations are intended to be covered by the following claims.

We claim:

1. A female contraceptive device comprising:
   a rim defining a loop, said rim having a first end and a second end, said rim along said first end having a generally concave configuration in a first axial direction; and
   a barrier portion extending across said loop, said barrier portion including a cervical dome which opens generally in said first axial direction.

2. A female contraceptive device in accordance with claim 1 in which said rim along said second end has a generally concave configuration in a second axial direction which is generally opposite to said first axial direction.

3. A female contraceptive device in accordance with claim 2 in which said rim comprises a pair of bands, a spring surrounding said bands and joining said bands together at their respective ends, and a cover enclosing said spring.

4. A female contraceptive device in accordance with claim 3 wherein each of said bands has a generally sinusoidal S shaped configuration.

5. A female contraceptive device in accordance with claim 4 wherein each of said bands comprises three arcs, each of said three arcs having a different radius and an alternating aspect.

6. A female contraceptive device in accordance with claim 5 wherein a first of said arcs is generally concave upward with a radius of curvature of about 1.2 inches, a second of said arcs is generally concave downward with a radius of curvature of about 0.9 inches, and a third of said arcs is generally concave upward with a radius of curvature of about 1.9 inches.

7. A female contraceptive device in accordance with claim 1 wherein the rim conforms to the shape of a conic projection.

8. A female contraceptive device in accordance with claim 1 in which said barrier portion further includes a relatively flat membrane, wherein said membrane is adjacent said first end of said rim and said cervical dome is adjacent said second end of said rim.

9. A female contraceptive device in accordance with claim 8 in which said membrane includes an indicator disposed on a first surface of said membrane to indicate a proper insertion direction.

10. A female contraceptive device in accordance with claim 9 in which said indicator is embossed on said first surface.

11. A female contraceptive device in accordance with claim 1 in which said barrier portion further includes a removal dome which opens generally in a second axial direction which is generally opposite to said first axial direction.

12. A female contraceptive device in accordance with claim 1 in which said rim further includes at least one loop extending generally radially outwardly from said first end.

13. A female contraceptive device in accordance with claim 1 wherein said rim comprises a plurality of projections extending generally outwardly in a radial direction.

14. A female contraceptive device in accordance with claim 13 wherein said projections have a generally domed shape configuration.

15. A female contraceptive device comprising:
a rim defining a loop, said rim having a first end and a second end; and
a barrier portion extending across said loop, said barrier portion including a cervical dome which opens generally in a first axial direction, and said rim along said second end having a generally concave configuration in a second axial direction opposite to said first axial direction.

16. A female contraceptive device in accordance with claim 15 in which said barrier portion further includes a relatively flat membrane, wherein said membrane is adjacent said first end of said rim and said cervical dome is adjacent said second end of said rim.

17. A female contraceptive device in accordance with claim 15 wherein said barrier portion further includes a removal dome which opens generally in said second axial direction.

18. A female contraceptive device comprising:
a rim defining a loop, said rim having a first end and a second end; and
a barrier extending across said loop, said barrier including a relatively flat membrane adjacent said first end of said rim and a cervical dome adjacent said second end of said rim.

19. A female contraceptive device in accordance with claim 18 wherein said barrier portion further includes a removal dome which opens generally in an axial direction.

20. A female contraceptive device comprising:
a rim defining a loop, said rim having contours to form a non-planar configuration which generally conforms to a conic projection; and
a barrier extending across said loop, said barrier including a cervical dome opening generally in a first axial direction.

21. A female contraceptive device in accordance with claim 20 in which said rim along said first end has a generally concave configuration in said first axial direction and along said second end has a generally concave configuration in said second axial direction.

22. A female contraceptive device in accordance with claim 21 in which said rim comprises a pair of bands, a spring surrounding said bands and joining said together at their respective ends, and a cover enclosing said spring, wherein each of said bands comprise three arcs, each of said arcs having a different radius and an alternative aspect.

23. A female contraceptive device in accordance with claim 20 wherein said barrier portion further includes a removal dome which opens generally in said second axial direction.

* * * * *